United States Patent
Shalaby et al.

(10) Patent No.: US 9,006,278 B2
(45) Date of Patent: Apr. 14, 2015

(54) CONTROLLED RELEASE SYSTEMS OF PLURIBIOACTIVE ANTIFUNGAL DRUGS AND APPLICATIONS THEREOF

(75) Inventors: Shalaby W. Shalaby, Anderson, SC (US); Georgios T. Hilas, Anderson, SC (US); Sheila Nagatomi, Seneca, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 12/931,327

(22) Filed: Jan. 29, 2011

(65) Prior Publication Data

US 2012/0077823 A1 Mar. 29, 2012

Related U.S. Application Data

(60) Provisional application No. 61/337,303, filed on Feb. 2, 2010.

(51) Int. Cl.
| | | |
|---|---|---|
| *A01N 43/50* | (2006.01) | |
| *A61K 31/415* | (2006.01) | |
| *A61K 31/497* | (2006.01) | |
| *A61K 31/496* | (2006.01) | |
| *A61K 31/4174* | (2006.01) | |
| *A61K 31/506* | (2006.01) | |
| *A61K 31/7048* | (2006.01) | |

(52) U.S. Cl.
CPC ........... *A61K 31/496* (2013.01); *A61K 31/4174* (2013.01); *A61K 31/506* (2013.01); *A61K 31/7048* (2013.01)

(58) Field of Classification Search
USPC ............................................ 514/399, 254.06
See application file for complete search history.

(56) References Cited

U.S. PATENT DOCUMENTS

| | | | | |
|---|---|---|---|---|
| 5,624,704 A | * | 4/1997 | Darouiche et al. ........... | 427/2.24 |
| 2008/0069850 A1 | * | 3/2008 | Shalaby et al. ............... | 424/405 |

FOREIGN PATENT DOCUMENTS

WO WO 2006065873 A2 * 6/2006

OTHER PUBLICATIONS

Sheehan et al. Clinical Microbioloy Reviews, 1999, vol. 12, Issue, pp. 40-79.*

* cited by examiner

*Primary Examiner* — Samir Jean-Louis
(74) *Attorney, Agent, or Firm* — McNair Law Firm, P.A.; Douglas L. Linberry

(57) ABSTRACT

Controlled release systems release at least one pluribioactive antifungal drug exhibiting at least one additional bioactivity from the group consisting of spermiostatic, antineoplastic, antibacterial, antirestenotic and antiviral activities. The drug release system is designed for use as a spermiostatic contraceptive, intravaginal ringed-mesh which may also exhibit antiviral activity, an in situ-forming implant for treating different forms of cancer and topical film for treating or preventing bacterial and fungal infections.

7 Claims, No Drawings

US 9,006,278 B2

CONTROLLED RELEASE SYSTEMS OF PLURIBIOACTIVE ANTIFUNGAL DRUGS AND APPLICATIONS THEREOF

The present application claims priority to provisional application U.S. Ser. No. 61/337,303, filed Feb. 1, 2010.

FIELD OF THE INVENTION

This invention is directed towards controlled release systems for pluribioactive drugs with established antifungal activities, but further exhibit at least one additional bioactivity or a plurality of bioactivities selected from the group consisting of those associated with spermiostatic, antineoplastic, antibacterial, and antirestenotic effects. A major aspect of this invention deals with azole-type antifungal drugs, which are practically insoluble in water and display spermiostatic, antineoplastic and antirestenotic activities with and without being part of at least one absorbable controlled delivery system.

BACKGROUND OF THE INVENTION

Paclitaxel is a well-established antineoplastic agent which is commonly used for treating breast, lung, and ovarian cancers. In recent years, paclitaxel was successfully used as part of a drug-eluting endovascular stent for managing vascular restenosis following angioplasty. Similarly, rapamycin, a well-established immunosuppressant is used in a drug-eluting stent as an antirestenotic drug. The dual function nature of these two drugs led to our use of the term pluribioactive drugs as they exhibit at least two pharmacological functions and are expected to continue adding to their portfolio beyond two bioactivities toward being pluribioactive. An old drug with the potential of being denoted a pluribioactive agent is aspirin, which is a well-established analgesic drug which has become widely used to prevent platelet aggregation. Unfortunately, the most effective drugs for treating fungal infections have never been considered for being a pluribioactive drug. And this provided the incentive to pursue the study associated with the instant invention to demonstrate, unexpectedly, that certain antifungal drugs do exhibit at least two types of bioactivities beyond their well-established role as antifungal agents.

SUMMARY OF THE INVENTION

This invention generally deals with a controlled release system of at least one pluribioactive antifungal drug exhibiting at lease one additional bioactivity selected from the group consisting of spermiostatic, antineoplastic, antibacterial, antirestenotic and antiviral activities, wherein at least one pluribioactive antifungal drug is selected from the group consisting of miconazole, ketoconazole, itraconazole, voriconazole, and amphotericin B, and wherein the pluribioactive antifungal drug is miconazole or ketoconazole and the drug release system comprises a spermiostatic contraceptive biostable intravaginal ringed-mesh.

From a clinical perspective, this invention deals with a controlled release system of at least one pluribioactive antifungal drug exhibiting at lease one additional bioactivity selected from the group consisting of spermiostatic, antineoplastic, antibacterial, antirestenotic and antiviral activities, wherein the pluribioactive antifungal drug is miconazole or ketoconazole and the drug release system comprises an absorbable in situ-forming polymeric implant in the form of a vascular liner for preventing restenosis, and wherein the pluribioactive antifungal drug is miconazole or ketoconazole and the drug release system comprises an absorbable in situ-forming polymeric implant for treating at least one type of cancer selected from the group consisting of ovarian, breast, lung, cervical, liver and pancreatic cancers.

This invention also deals with a controlled release system of at least one pluribioactive antifungal drug exhibiting at lease one additional bioactivity selected from the group consisting of spermiostatic, antineoplastic, antibacterial, antirestenotic and antiviral activities wherein the pluribioactive antifungal drug is miconazole or ketoconazole and the drug release system comprises a spray-on absorbable in situ-formed film for preventing or treating topical bacterial and fungal infections, and wherein the pluribioactive antifungal drug is miconazole or ketoconazole and the drug release system comprises a surgical drape for preventing infection, and further wherein the pluribioactive antifungal drug is miconazole or ketoconazole and the drug release system comprises a biostable contraceptive, antiviral, antiretroviral, intravaginal ringed-mesh.

DETAILED DESCRIPTION OF PREFERRED EMBODIMENTS

Several major antifungal agents have been successfully used topically and/or systemically for many years. Among these agents are the imidazole, triazole and polyene types, which are administered systemically and/or topically. The polyene-type, amphotericin B, as well as the azole-type, fluconazole and itraconazole, are used systemically. Well-established antifungal agents manifest their bioactivity on organisms by (1) inhibiting cell synthesis and activating enzymes that destroy the cell wall; (2) increasing cell membrane permeability; (3) interfering with protein synthesis; and/or (4) interfering with nucleic acid metabolism. These impressive modes of action as antifungal agents are not paralleled by any effective use of these agents for indications beyond treating or preventing fungal infection. Acknowledging this fact and recognizing recent use of the antineoplastic drug, paclitaxel, and immunosuppressant drug, rapamycin, as antirestenotic agents, (denoted herein as pluribioactive agents), and the essentially common use of the analgesic drug, aspirin, as an anti-platelet aggregation agent, prompted our interest in exploring the use of established antifungal drugs as pluribioactive agents, which may exhibit at least one additional bioactivity. In effect, we were to examine these antifungal agents for effectiveness as antineoplastic, antibacterial, antirestenotic and spermiostatic agents as part of controlled release systems. Accordingly, this invention deals with absorbable or non-absorbable controlled release polymeric systems containing at least one antifungal drug for clinical uses in pluribioactive modes.

Of the pluribioactive drugs and controlled release systems therefor, those containing essentially water-insoluble azole-type drugs are of special importance. More specifically, this invention deals with absorbable and non-absorbable polymeric drug release systems centering on the antifungal agents, miconazole or ketoconazole, and their effectiveness in manifesting at least one additional function selected from those associated with (1) treating or preventing bacterial infection; (2) treating or preventing different types of cancer; (3) preventing or retarding vascular restenosis following angioplasty; (4) intravaginal contraception; (5) preventing and treating viral and retroviral infection; and (6) intravaginal contraception (through spermiostatic effects) while preventing or treating viral and retroviral infections.

Further illustrations of the present invention are provided by the following examples:

Example 1

Preparation of Miconazole and Ketoconazole Solutions and Evaluation of Their Efficacy as Pluribioactive Drugs To examine the effect of miconazole and ketoconazole on cancer cells (SKOV3, OVCAR3, and MCF7) and vascular cells (human aortic smooth muscle and umbilical vein endothelium), each cell type was seeded in separate 24-well plates at a density of approximately 50,000 to 100,000 cells/cm$^2$. After incubation under standard cell culture conditions (that is, a 37° C., humidified, 5% $CO_2$ environment) for approximately 24 hours, media was aspirated from each well, and replaced with the appropriate treatments. Miconazole or ketoconazole was dissolved in ethanol to create a stock solution. A portion of the stock solution (up to 2% by volume) was then added to complete media which resulted in the concentrations shown in the table below. The same volume of ethanol was added to control wells, but no drug was present. Cells were further incubated for 2 days. At that time, cell viability was measured using a commercially available kit, according to manufacturer instructions (CellTiter 96® AQ$_{ueous}$ One Solution Cell Proliferation Assay, Promega). All samples were prepared in triplicate. Percent inhibition was then calculated using the absorbance values.

Bacterial and fungal cultures (*Staphylococcus aureus* and *Candida albicans*) were maintained according to manufacturer (ATCC) instructions. Broth was inoculated according to 0.5 McFarland standard (0.05 absorbance reading). Miconazole or ketoconazole was dissolved in ethanol to create a stock solution. A portion of the stock solution was then added to the appropriate broth which resulted in the concentrations shown in the table below. Cultures were incubated overnight (approximately 16 hours), at which time relative absorbance was recorded for each sample using a spectrophotometer (600 nm wavelength). Absorbance values were then used to calculate percent inhibition.

$M_n$=400 Da) (88.0 grams, 0.22 moles) was charged into a 500 mL reaction flask under vacuum (<0.5 mmHg) for a period of one hour at 100° C. The remainder of the synthesis was carried out under a nitrogen blanket. Glycolide (22.1 grams, 0.19 moles), DL-lactide (109.9 grams, 0.76 moles), and tin (II)-2-ethythexanoate (0.397 mL of a 0.2M solution in toluene, 7.948×10$^{-5}$ moles) were added to the reaction mixture while stirring at 120 rpm. The temperature was raised to 140° C. for 14.5 hours and then taken to room temperature. 1,6-Diisocyanatohexane (29.6 grams, 0.176 moles) was added in 8 aliquots and stirred at 120 rpms. The temperature was raised to 100° C. and maintained for 1 hour after which the temperature was lowered to 60° C. Tetrahydrofuran (THF) (249.6 grams, 3.462 moles) was added while stirring at 120 rpms until the entire polymer was dissolved. Isopropanol (7.333 mL, 0.096 moles) was then added to the reaction flask and stirred at 120 rpms for 1 hour. The polymer solution was slowly poured into a 2000 mL beaker containing ~700 mL of water and 300 grams of ice while stirring with a spatula. The water was decanted and the polymer was added to a 1000 mL flask. The flask was then transferred to a rotary evaporator and placed under vacuum (<0.5 mm Hg). The polymer was dried at 55° C. for 16 hours followed by 80° C. for 2 hours on the rotary evaporator.

The polymer synthesized above was characterized by THF GPC for molecular weight. The resultant $M_n$ was 8.20 kDa.

Example 3

Preparation of a Bioactive In Situ-Forming Absorbable Polyether-Ester-Urethane-Based Implant and Monitoring the Release Profile of Miconazole Therefrom To create an in situ-forming absorbable polyether-ester-urethane based implant the following steps were pursued. An absorbable polyether-ester-urethane-based polymer (3.50 grams), as described in Example 2, was weighed into a 20 mL glass vial. An acetylated polyethylene glycol (G4A, $M_n$=4.0 kDa) (1.50 grams) was added to the vial to yield a formulation consisting of 70% polyether-ester-urethane-based polymer

|  |  | % Inhibition* | | | | | |
|---|---|---|---|---|---|---|---|
|  |  |  |  | Mammalian Cell Lines | | | |
|  | Drug | Bacteria/Fungi | | Ovarian Cancer | Ovarian Cancer | Breast Cancer | Smooth |  |
| Drug | Concentration | C. albicans | S. aureus | (SKOV3) | (OVCAR) | (MCF7) | Muscle | Endothelial |
| Miconazole | 20 µg/mL | 98.3% | 76.7% | 13% | 19% | 19% | 58% | 18% |
|  | 60 µg/mL | 73.2% | 65.0% | 61% | 57% | 55% | 84% | 58% |
| Ketoconazole | 40 µg/mL | 93.8% | 32.7% | 0% | 0% | 58% | 31% | 16% |
|  | 80 µg/mL | 98.6% | 67.6% | 51% | 57% | 50% | 68% | 38% |

*Percent (%) Inhibition was calculated as follows: (Control value − Treatment value)/Control value

Example 2

Preparation of a Typical Absorbable Polyether-Ester-Urethane-Based Composition as a Drug Vehicle for Bioactive In Situ-Forming Implants To prepare a typical absorbable polyether-ester-urethane-based composition for use as a drug matrix for a bioactive in situ-forming implant the procedure outlined in U.S. patent application Ser. Nos. 11/453,207 and 11/820,849 was followed. Weighed out poly(ethylene glycol) (PEG 400, and 30% G4A. This mixture was purged with nitrogen gas and placed into a 90° C. oven. After 10 minutes the mixture was removed from the oven and stirred with a spatula for approximately 30 seconds, after which the vial was once again purged with nitrogen gas and placed back into a 90° C. oven. This mixing procedure was repeated a total of five times to obtain a homogenous mixture. Miconazole nitrate (50 mg or 200 mg) was then added to this formulation to create a drug matrix consisting of 1% or 4% miconazole, respectively. This was stirred with a spatula until the drug was uniformly dispersed.

To study the release profile of miconazole, 1.00 gram of the formulation produced above was transferred to a 20 mL glass vial containing 5.00 mL water. The vial was then placed into a 37° C. incubator for 24 hours after which the eluent was collected and tested via HPLC to determine amount of miconazole released. Following testing, 5 mL of fresh water was added back into the vial to continue the release study. The release study was continued every day for a total of 21 days and the results can be seen below in Table I.

TABLE I

Miconazole Release Profile from a Drug Loaded Polyether-ester-urethane-based Implant.

| Time Period (Days) | Total Drug Released* (mg) | | Cumulative Drug Released (mg) | | % Cumulative Drug Released | |
|---|---|---|---|---|---|---|
| | 1% Miconazole | 4% Miconazole | 1% Miconazole | 4% Miconazole | 1% Miconazole | 4% Miconazole |
| 1 | 1.208 | 0.994 | 1.21 | 0.99 | 11.2 | 2.36 |
| 7 | 0.315 | 1.087 | 3.62 | 4.54 | 33.5 | 10.77 |
| 21 | 0.151 | 1.240 | 5.05 | 12.08 | 46.7 | 28.69 |

*These values show the amount of drug released in the previous 24 hours. For example, for "Day 7", this is the amount released between Day 6 and Day 7.

TABLE II

Miconazole Concentration in Daily Eluents Released from a Drug Loaded Polyether-ester-urethane-based Implant.

| Time Period (Days) | Concentration of Miconazole eluents (µg/mL) | |
|---|---|---|
| | 1% Miconazole | 4% Miconazole |
| 1 | 0.242 | 0.199 |
| 7 | 0.063 | 0.217 |
| 21 | 0.030 | 0.248 |

*These values show the concentration of miconazole in the eluent collected after 24 hours of incubation. For example, for "Day 7", this is the concentration of miconazole found after fresh water was added to the drug-loaded polymer on Day 6 and incubated for 24 hours.

Example 4

Preparation of a Typical Low-Crystallinity Polyaxial Segmented Absorbable Polyester-Based Composition and Evaluation as a Drug Vehicle for the Controlled Release of Miconazole and Ketoconazole The polymer was prepared using the general procedure for the synthesis of crystalline, segmented, polyaxial copolyesters as described earlier (U.S. Pat. No. 7,348,364 and U.S. patent application Ser. No. 11/598,427). An amorphous polymeric initiator comprising 35/14/9 (molar) ε-caprolactone/trimethylene carbonate/glycolide was made and end-grafted to form crystalline eng-grafts comprising 42/2 (molar) l-lactide/glycolide to yield a copolyester made of 35/14/34/17 (molar) caprolactone/trimethylene carbonate/l-lactide/glycolide. The polymer was characterized for identity (IR, NMR), molecular weight (in terms of inherent viscosity), and thermal property (DSC). It was shown to have an inherent viscosity of 1.45 dL/g, melting temperature of 109° C., and heat of fusion of 7.4 J/g. A liquid formulation of CP-1 with acetylated polyethylene glycol-400 was prepared and shown to be well-suited for incorporating miconazole and ketoconazole. Upon exposure of the triclosan formulation to a buffered medium at pH 7.2 and 37° C., the hydroformed film provided a sustained drug release for at least one week.

Example 5

Preparation of a Crystalline Polyaxial Segmented Polyester-Based Composition for Use as a Vehicle for the Controlled Release of Miconazole and Ketoconazole The polymer was prepared following the procedure for the synthesis of the copolymer of Example 4 with the exception of using the following: an amorphous polymeric initiator made from 1/80/20 mmole trimethyl propane/p-dioxanone/glycolide end-grafted with p-dioxanone (1000 mmole) in the presence of stannous octanoate as a catalyst (0.01 mmole added initially) at a reaction temperature in the two-step reaction of 80° C. for 6 and then 56 hours. The polymer was isolated and purified by dissolving acetone and precipitating in cold water. The purified polymers was dried to a constant weight and characterized by GPC and DSC to show an $M_n$=70, kDa and $T_m$=70° C.

Example 6

Correlation of the Pluribioactive Effects of Aqueous Drug Solutions/Microdispersion of Miconazole with the Drug Release Profile from Polymeric Vehicles The data noted in Example 1 show that solutions/microdispersions of miconazole of 40 to 60 µg/mL are 57% to 84% effective in inhibiting the growth of the examined cell line of bacteria, yeast, ovarian cancer, breast cancer and smooth muscle cells. Meanwhile, the miconazole release data from a typical polyether-ester-based implant, shown in Example 2, show that miconazole continued to release for at least 21 days. Using the proper polymeric vehicle and concentrations of the drug therein, it can be demonstrated that not only aqueous solutions/microdispersions of miconazole are effective as pluribioactive systems but also polyether-ester urethane-based controlled release systems loaded with micronazole.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A method for treating bacterial infections comprising:
   employing an antifungal drug selected from the group consisting of miconazole, ketoconazole, itraconazole, voriconazole, and amphotericin B, the antifungal drug exhibiting antibacterial activity, wherein the antifungal drug is introduced into the body by means of a drug release system consisting of an absorbable polymeric implant having the antifungal drug incorporated therein; and
   wherein the absorbable polymeric implant consists of a polyether-ester-urethane copolymer of polyethylene glycol, glycolide and DL-lactide.

2. A method for treating bacterial infections comprising:
   employing an antifungal drug selected from the group consisting of miconazole, ketoconazole, itraconazole, voriconazole, and amphotericin B, the antifungal drug exhibiting antibacterial activity, wherein the antifungal drug is introduced into the body by means of a drug release system consisting of an absorbable polymeric implant having the antifungal drug incorporated therein; and
   wherein the absorbable polymeric implant consists of polyethylene glycol.

3. A method for treating bacterial infections comprising:
   employing an antifungal drug selected from the group consisting of miconazole, ketoconazole, itraconazole, voriconazole, and amphotericin B, the antifungal drug exhibiting antibacterial activity, wherein the antifungal drug is introduced into the body by means of a drug release system consisting of an absorbable polymeric implant having the antifungal drug incorporated therein; and
   wherein the absorbable polymeric implant consists of 70 weight-% polyether-ester-urethane and 30 weight-% polyethylene glycol.

4. The method of claim 1 wherein the absorbable polymeric implant comprises a copolymer of 0.22 moles of polyethylene glycol, 0.19 moles of glycolide, and 0.76 moles of DL-lactide.

5. The method of claim 1 wherein the antifungal drug is miconazole.

6. The method of claim 3 wherein the antifungal drug is miconazole.

7. The method of claim 4 wherein the antifungal drug is miconazole.

* * * * *